(12) United States Patent
Chevalier

(10) Patent No.: US 6,664,049 B1
(45) Date of Patent: Dec. 16, 2003

(54) METHOD AND DEVICE FOR CELL LYSIS

(75) Inventor: Michel Chevalier, Beaurepaire (FR)

(73) Assignee: Aventis Pasteur S.A., Lyons Cedex (FR)

( * ) Notice: Subject to any disclaimer, the term of this patent is extended or adjusted under 35 U.S.C. 154(b) by 0 days.

(21) Appl. No.: 09/600,664

(22) PCT Filed: Jan. 20, 1999

(86) PCT No.: PCT/FR99/00105

§ 371 (c)(1),
(2), (4) Date: Mar. 21, 2001

(87) PCT Pub. No.: WO99/37750

PCT Pub. Date: Jul. 29, 1999

(51) Int. Cl.$^7$ .............................. C12Q 1/68; C12M 1/34; C07H 19/00
(52) U.S. Cl. ..................... 435/6; 435/287.2; 435/287.3; 536/22.1
(58) Field of Search ....................... 435/6, 40.5, 287.2, 435/287.3, 22.1

(56) References Cited

U.S. PATENT DOCUMENTS 4,294,824 A * 10/1981 Jones et al. .................. 424/101

2001/0034435 A1 * 10/2001 Nochumson et al. ...... 536/23.1

FOREIGN PATENT DOCUMENTS

| WO | WO 90/11092 | | 10/1990 |
|---|---|---|---|
| WO | WO 96/02658 | | 2/1996 |
| WO | WO 96/02658 A1 | * | 2/1996 |
| WO | WO 96/36106 | | 11/1996 |
| WO | WO 97/23601 | * | 7/1997 |
| WO | WO-97/23601 A1 | * | 7/1997 |
| WO | WO 99/37750 | | 7/1999 |

OTHER PUBLICATIONS

Birnboim, (1983) *Methods in Enzymology*, vol. 100, 243–255.

* cited by examiner

Primary Examiner—Jeffrey Fredman
Assistant Examiner—Suryaprabha Chunduru
(74) Attorney, Agent, or Firm—McDonnell Boehnen Hulbert & Berghoff

(57) ABSTRACT

Method and device for cell lysis in which a liquid mixture of bateria or eukaryoptic cells and of a lysing agent is produced continuously, and this mixture is caused to flow immediately in a steady stream inside a tubing (7), the flow rate of this stream being adjusted as a function of the diameter and of the length of the tubing (7) so as to obtain a substantially homegenous cell lysate at the outlet (8) of the said tubing.

32 Claims, 1 Drawing Sheet

METHOD AND DEVICE FOR CELL LYSIS

CROSS-REFERENCES TO RELATED APPLICATIONS

Figure 1:
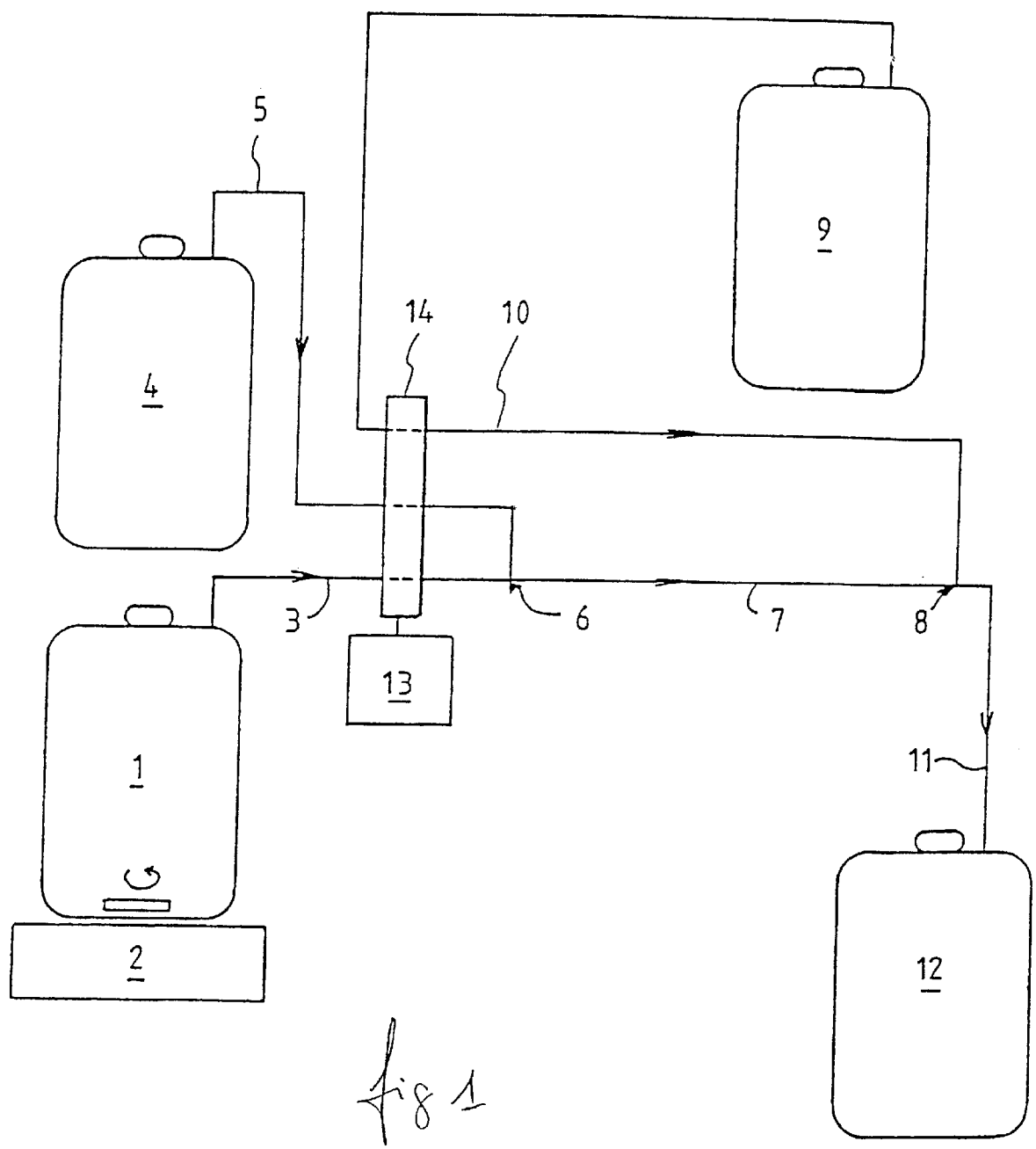

This application claims right of priority to WO 99/37750 filed Jan. 20, 1999.

STATEMENT REGARDING FEDERALLY SPONSORED RESEARCH OR DEVELOPMENT

Not Applicable

FIELD OF THE INVENTION

The present invention relates to a method and a device for lysing bacteria or eukaryotic cells, as well as for extracting and purifying nucleic acids, and in particular plasmids, from bacteria or eukaryotic cells containing these plasmids.

SUMMARY OF RELATED ART

The production of plasmids of interest, and in particular of plasmids into which a gene or a coding sequence of DNA has been inserted, is achieved by making a multicopy of these plasmids in bacteria capable of producing a large number of these plasmids, and in particular in certain strains of *Escherichia coli* which are high plasmid producers and which are often already used in the laboratory or on an industrial scale.

One of the applications which requires major production of a plasmid, on an industrial scale, is the manufacture of medicaments or vectors of prophylactic or therapeutic interest based on a naked plasmid or a plasmid combined with means for penetrating into the cells of the recipient host. Such applications are described for example in Patent Application WO 90/11092.

Several techniques exist for bacterial lysis which allow the extraction of the plasmids, followed by a separation, and therefore by a purification of these plasmids. The technique most commonly used is the alkaline lysis technique which uses an alkaline lysing agent such as a sodium hydroxide+ SDS (sodium dodecyl sulphate) preparation, followed by neutralization with an acidic agent such as potassium acetate. This neutralizing agent also has the effect of precipitating all the bacterial constituents including the genomic DNA, the supernatant containing essentially the plasmid DNA. The supernatant may then be separated from the precipitate by centrifugation or filtration (Birnboim Methods In Enzymology (1983) 100:243). The alkaline lysis technique is most particularly recommended for lysing bacteria; however, it can be used equally well for lysing eukaryotic cells.

This technique, which is suitable on a laboratory scale, is difficult to carry out on an industrial scale because the lysate resulting from the action of the alkaline agent on the bacteria constitutes a very viscous suspension, such that the lysate being formed has to be homogenized by stirring. Likewise, after neutralizing with acid, homogenization by stirring is required. This stirring is delicate and it is generally carried out manually, the operator gently stirring the bottles or flasks containing the lysis medium. An insufficient stirring results in a lysis of poor quality whereas an excessive stirring tends to fragment the genomic DNA, which subsequently mixes with the plasmids. In both cases, a reduction in the plasmid DNA yield is observed. Consequently, the dexterity of the operator is an essential requirement for the success of the operation. In order to automate the method of lysis, it has already been proposed in the document WO 97/23601 to continuously pass the suspension of cells to be lysed and a solution of a lysing agent through a static mixer of sufficient length in order to complete the lysis. The lysate resulting therefrom may then be conveyed through a tubing to a second static mixer, into which a solution of the precipitating agent also enters.

Such a method therefore uses a specific means, namely a static mixer, which replaces the manual stirring of large volumes by a continuous stirring over the whole length of the mixer. The use of such a mixer, in addition to requiring the purchase, maintenance and cleaning of the device, requires a fixed duration of contacting with the lysing agent, with no practical possibility of controlling it or of varying it. Furthermore, the stirring maintained in the mixer, even if it is preferable to the poorly controlled mixing of batch volumes, can cause breaks in or degradation of cellular constituents and in particular of nucleic acids.

Another method, described for example in the document WO 96/36106, also makes it possible to establish a continuous lysis, but this time without using stirring means. This method consists (i) in preparing a mixture of a bacterial suspension and of an agent, such as lysozyme, in incubating this mixture for about one hour in order to make the bacterial wall fragile, and then (ii) in passing a stream of this mixture inside a tubing heated to a high temperature (70–100° C.). The action of the heat promotes the lysis. The disadvantage of such a solution is to require a means of heating at high temperatures and adjusting the temperature to the various specific cases which may be encountered.

SUMMARY OF THE INVENTION

The present invention is intended to overcome these disadvantages and to provide a method of cell lysis which is applicable in particular to the extraction and purification of nucleic acids such as plasmids from bacteria or eukaryotic cells, and which is capable of being used without manual intervention and under extremely inexpensive conditions.

Another objective of the invention is to provide a method which makes it possible to control extremely precisely the conditions and the duration of the lysis and of the extraction, this being for all the cells present.

Another objective is to provide a method which makes it possible to establish substantially homogeneous lysis conditions for a population of cells.

Another objective is to provide a method capable of being used in a closed medium, protected from contaminations, which is an advantage for the pharmaceutical quality of the desired products, for example plasmids.

Another objective is to obtain a reduction in the duration of the cell/lysing agent contact which is necessary for completing the lysis.

Another objective is to provide a device for carrying out this method, a device which is simple and not very expensive.

Another objective is to provide on the industrial scale plasmid preparations with a high and substantially enhanced yield compared to that for preparations which may be obtained according to the prior art methods.

DETAILED DESCRIPTION OF THE INVENTION

The invention is based on the unexpected discovery that it is possible, provided a number of parameters are observed, to bring about a homogeneous and controlled lysis of cells, and in particular of bacteria, by simple continuous mixing, in a common tubing, of a suspension of cells with a lysing agent, in spite of the expected high viscosity, without using any of the prior art means such as a static mixer or high temperatures.

The subject of the invention is therefore a method of cell lysis in which a liquid mixture of cells and of a lysing agent is produced continuously, and this mixture is caused to flow immediately in a steady stream inside a tubing, the flow rate of this stream being adjusted as a function of the diameter and of the length of the tubing so as to obtain a substantially homogeneous cell lysate at the outlet of the said tubing.

The production of a homogeneous lysate results in a substantial drop in turbidity and the appearance of a mixture which is transparent to the eye.

Preferably, the tubing has a small inner diameter so that the mixture forms almost instantly in a homogeneous manner, without separate liquid veins being formed. This diameter may be determined experimentally. In general, a diameter of the order of 1 cm or preferably less satisfies this definition, and a diameter of between 2 and 8 mm is preferred.

It should quite obviously be understood that if the diameter and the flow rate of the stream are process parameters which are set in advance, the length of the tubing can equally be adjusted so as to obtain the desired effect. For example for a diameter and a given flow rate of the stream, it is sufficient to vary the length of the tubing e. g., using a simple flexible tubing which is cut to the desired length.

The minimum length of the tubing from the cell suspension and lysing agent meeting point, over which it is necessary to travel in order to achieve the state of lysis, can be easily determined by simply observing through a transparent tubing the reduction in the turbidity of the mixture until the appearance of a lysate which is transparent to the eye. A tubing length of the order of 10 cm to a few meters is in general suitable.

One of the advantages of the invention consists in the homogeneity of the mixture during lysis (the duration of the lysis is substantially identical for all the bacteria); which makes it possible to obtain in fine a homogeneous lysate. This is achieved by the suitable choice of the parameters of the invention (diameter, and length of tubing, flow rate of the stream) without using stirring or heating means.

Preferably, the mixing of cells and of lysing agent is carried out by introducing into the above-mentioned tubing a stream of cells, for example of a cell suspension, and a stream of a solution of lysing agent, such that the flow of the stream of this mixture produces a rapid homogenization, which is practically instantaneous, if a tubing having a reduced diameter is used.

The lysing agent may be a chemical agent, for example an alkaline agent such as a sodium hydroxide+SDS solution, preferably a 0.2 M NaOH/1° s SDS mixture. This may also be a solution which is hypotonic relative to the cell medium, intended to cause an osmotic shock. In the case where the bacteria are simply transferred into a hypotonic solution, they have been treated beforehand so that their wall is made fragile, with an agent such as lysozyme. The treatment with an alkaline agent is particularly suited to bacterial lysis, whereas the treatment with a hypotonic solution is appropriate most particularly for the lysis of eukaryotic cells.

In the case where an alkaline lysing agent is used, the addition to the lysate of a neutralizing agent is preferred. Indeed, the addition of this agent makes it possible to stop the degrading action linked to the alkaline agent, once a complete and homogeneous lysis has been obtained. In the latter case, another advantage of the invention consists in controlling the duration during which the cells are subjected to highly alkaline pH conditions. This makes it possible to very easily implement the optimum duration conditions leading to a complete and homogeneous lysis by avoiding prolonging the action of the alkaline agent beyond the time necessary and sufficient to complete the lysis in order to avoid any deleterious action on the DNA in particular. The neutralizing agent which is added to the lysate arriving at the end of the tubing may be preferably sodium or potassium acetate, for example 3 M potassium acetate. It is advantageously chosen so as to obtain a final pH of close to 5.5 by means of the addition of 12 N HCl.

Moreover, if the aim pursued in fine consists e.g. in extracting plasmids, it is desirable to separate these plasmids from the rest of the cellular constituents. This separation is achieved by precipitating these cellular constituents, including the genomic DNA, by adding a precipitating agent to the lysate, the plasmids then remaining in the supernatant. As precipitating agent, there may be used sodium or potassium acetate, for example 3 M potassium acetate. It is advantageously chosen so as to obtain a final pH of close to 5.5 by means of the addition of 12 N HCl.

A precipitating agent such as sodium or potassium acetate also serves as neutralizing agent, when the alkaline lysis technique is used.

The subject of the invention is also a method of extracting and/or purifying nucleic acids, in particular plasmids, from a cell suspension, in which (i) the method of lysis according to the invention is used in order to obtain a cell lysate and, continuously after the method of lysis, (i) the cell lysate is treated with a precipitating and/or neutralizing agent in order to obtain a preparation comprising a supernatant containing the plasmid DNA and a precipitated or flocculated phase containing the majority of the cellular components including the genomic DNA. To do this, advantageously, (i) there is produced, continuously, a mixture of a cell suspension and of a liquid preparation (solution) of a lysing agent, at a first determined meeting point, from which a steady stream of the said mixture is established in a tubing, in order to homogenize the mixture of the suspension and of the lysing agent, (ii) this mixture is maintained in this steady stream for a determined duration, and at the end of this duration (iii) a solution of a precipitating agent is added at a second determined meeting point, the said duration being determined by the distance separating the said first and second meeting points and by the speed at which the mixture moves (or linear flow rate) over this distance. Once the precipitation has been performed the plasmids remaining in the supernatant are separated in any manner from the rest of the precipitated or flocculated cellular components.

This plasmid extraction method can be advantageously used in the following manner:
(i) a stream of the cell suspension is established in a first tubing;
(ii) a stream of the lysing agent in solution is established in a second tubing which flows into the first tubing (or vice versa) at a first meeting point to form a third tubing;
(iii) a stream of a precipitating agent is established in a fourth tubing which flows into the third tubing (or vice versa) at a second meeting point situated downstream of the first meeting point, to form a fifth tubing;
(iv) a stream of the cell/lysing agent mixture produced at the first meeting point is established in the third tubing (between the first and second meeting point) at a linear flow rate adjusted as a function of the diameter and of the length of the third tubing, so as to allow the homogenization of the mixture and the production of a substantially homogeneous cell lysate at the second meeting point; and (v) in the fifth tubing, a stream of the preparation obtained at the second meeting point is established by mixing the cell lysate with the precipitating agent; and (vi) a preparation comprising a supernatant containing the plasmid DNA and a precipitated or flocculated phase containing the majority of the cellular components including the genomic DNA is recovered at the outlet of the fifth tubing.

Subsequently, it is possible in addition to carry out, in any manner, the separation of the supernatant from the precipitated or flocculated phase, preferably continuously after the recovery step (vi).

The following table indicates, by way of example, various experimental conditions (length of tubing, diameter, flow rate, duration of contact with the alkaline lysing agent) which make it possible to obtain a complete and homogenous bacterial lysis, by the alkaline lysis technique. The bacterial and lysing agent concentrations remain identical from one test to another.

| Tubing length | Diameter | Flow rate | Duration of contact with the lysing agent |
|---|---|---|---|
| 28 cm | 0.3 cm | 160 ml/min | 2 seconds |
| 26 cm | 0.7 cm | 160 ml/min | 15 seconds |
| 85 cm + reservoir of 500 ml | 0.7 cm | 160 ml/min | 4 minutes |

The time required to obtain a complete and homogeneous lysis, taking into account the customary proportions of suspension and of lysing agent, may be very substantially reduced and even less than one or several minutes, for example 5 min, and even brought to values as low as one or two seconds, in contrast with the approximately ten minutes necessary in the prior art.

It should also be understood that lysis, precipitation and/or neutralization conditions which are completely homogeneous over time are achieved, by means of the invention, over the entire cell suspension which is caused to flow through the tubing.

The ratio of the flow rates, and therefore of the volumes mixed, preferably corresponds to the following definitions:
bacterial suspension/lysing agent (for example sodium hydroxide+SDS mixture): between ¼ and ¾, and preferably of the order of ½,
alkaline lysing agent/acidic neutralizing agent, preferably potassium acetate: between 1 and 2 and preferably of the order of 1.3.

Preferably, the concentration of the bacterial suspension is of the order of 170 grams (as wet weight of bacteria)/liter of a conventional buffer (for example Tris EDTA)+glucose.

Preferably, the cell suspension is stored at low temperature and conveyed at this same temperature in the tubing towards the meeting point with the lysing agent, this temperature being preferably of the order of 4° C. The lysing agent may be maintained and transported at room temperature and the precipitating and/or neutralizing agent is preferably maintained at low temperature, such as 4° C.

The subject of the invention is also a device for carrying out this method, characterized in that it comprises,
from a cell suspension source, such as a reservoir, a tubing which makes it possible to establish a stream of cell suspension,
from a source of a lysing agent, such as a reservoir, a second tubing which makes it possible to establish a stream of the lysing agent, the said first and second tubings ending at a first meeting point at which they open into each other,
a third tubing having a small diameter and a determined length extending from the said first meeting point,
and means, such as pumping means, for establishing the streams in the said tubings;
the length, the diameter and the flow rate in the said third tubing being adjusted so as to obtain a substantially homogeneous mixture resulting in a substantially homogeneous lysate.

The device may, in addition, comprise:
from a neutralizing and/or precipitating agent source, such as a reservoir, a fourth tubing ending at a second meeting point at the end of the said third tubing such that the tubings open into each other, the said third tubing having a length determined by the distance between the said first meeting point and the said second meeting point;
from the said second meeting point, a fifth tubing having a small diameter, ending at recovery and/or separation means; and
and means, such as pumping means, for establishing the streams in the said fourth and fifth tubings.

Preferably, all the tubings have small diameters as defined above. The small diameters of the said tubings may be identical or different. The differences in diameter between tubings may be determined by the means for establishing the streams.

The means for establishing the streams may advantageously be pumps, preferably one or more peristaltic pumps which make it possible to establish in the various tubings the flow rate, and therefore, taking into account the diameters of the tubings, the desired speeds.

Advantageously, it is possible to use the same pump for the establishment of two or more streams, for example a peristaltic pump with several parallel channels, so as to ensure, including in the case of an untimely variation in the capacity of the pump, a constant proportionality between the said streams.

Of course, if the quantities to be treated are particularly large, the arrangement of the tubings according to the invention may be divided into two, tripled or multiplied, with preferably stream establishing means such as a pump, single or several pumps integrally attached so as to maintain, under any circumstance, a constant proportionality of the streams in each of the installations.

A tubing may open into another at the level of a meeting point at any angle. Generally, it is preferred that one of the tubings open substantially perpendicularly into the other but it is also possible to incline the axes of the openings.

Preferably, no particular means of homogenization such as a baffle or an obstacle in the tubing at the level of the meeting points, or means of heating which makes it possible to obtain high temperatures (greater than 60° C.), is provided.

Advantageously, the device according to the invention may comprise means for establishing and controlling temperatures so as to maintain the sources at the required temperatures. In particular, for the cell suspension, the installation may be arranged such that low temperature is maintained not only in the source but also in the first tubing up to the point where the lysis begins.

An installation according to the invention makes it possible, for example, to treat a volume of bacterial suspension of the order of 1 to 5 liters per hour.

The mixture obtained downstream of the first meeting point exhibits great homogeneity throughout the duration of the treatment, like the mixture neutralized downstream of the second meeting point, such that the separation means which make it possible to separate, on the one hand, the plasmids remaining in solution and, on the other hand, the other, precipitated or flocculated cellular components, work under constant conditions and contribute to the excellent reproducibility of the final purified plasmid preparation.

Moreover, the final yield, which may exceed 50 mg of plasmid per 100 g of bacteria, is considerably enhanced.

Other advantages and characteristics of the invention will emerge on reading the following description made by way of a nonlimiting example and referring to the accompanying drawing in which the sole figure represents a schematic view of a device for carrying out the method according to the invention.

The bacterial suspension to be lysed is a suspension obtained from a culture of a strain of *E. coli* in which a plasmid such as the plasmid pUC18 has been multiplied in Tris EDTA buffer with a bacterial concentration of the order of 200 g (wet weight) per liter.

The sodium hydroxide-SDS mixture is a 0.2 M NaOH/1o SDS mixture.

The potassium acetate solution used as neutralizing agent is at 3 M; pH 5.5.

The device represented in the figure comprises a first container 1 containing the bacterial suspension. This container is linked to means for maintaining a temperature of the order of +4° C. (not represented) and stirring means 2 which make it possible to maintain the homogeneity of the suspension.

From the source 1 extends a flexible silicone tubing having an inner diameter of 2.06 mm and forming the first tubing section 3.

The sodium hydroxide-SDS mixture is contained in a reservoir 4 from which extends a second tubing 5 having an inner diameter of 3.17 mm and made of the same flexible material. At position 6, where the first meeting point is located, the tubing 3 opens perpendicularly into the tubing 5 such that a mixture is formed at this position which causes rapid lysis of the bacteria. From point 6 extends a third tubing section 7 up to point 8 forming the second meeting point, the length of the tubing 7 being 0.8 meters. This tubing 7 has an inner diameter of 7 mm (variable).

The potassium acetate solution is contained in a reservoir 9 from which extends a fourth tubing 10 also made of flexible material and having an inner diameter of 2.79 mm opening into the tubing 7 at the meeting point 8, also perpendicularly to the tubing 7.

The container 9 is also linked to means for maintaining a low temperature +4° C.

From the second meeting point 8 extends a fifth tubing 11, formed by the extension of the tubing 7, this tubing 11 ending at a recovery reservoir 12.

It is understood that the diameters of the three tubings 3, 5 and 10 are in ratios such that the proportions of the inner sections of the tubings provide, for the same speed of circulation of the liquids, the desired proportions of mixture.

Consequently, the flexible tubings 3, 5 and 10 may pass through a single peristaltic pump 13 whose rotating part 14 ensures the establishment of the streams in the abovementioned proportions in the three tubings 3, 5 and 10.

The establishment of the flow rates in the desired proportions in the tubings 3, 5 and 10 of course determine the value of the flow rates downstream in the tubings 7 and 11.

The flow rates thus obtained are respectively 160 ml/min in 7 and 244 ml/min in 11.

The bacteria are subjected to the action of the sodium hydroxide+SDS mixture throughout the duration of travel of the liquid in the tubing 7, between points 6 and 8. This duration, in the example chosen, is 15 sec.

There is finally obtained, in the recovery container 12, a lysed preparation comprising two phases, namely a clear soluble phase containing the plasmids, substantially free of cellular component, and an insoluble top phase substantially containing the cellular components.

The separation of these two phases is then carried out by conventional filtration or centrifugation techniques and the purification of the plasmids may also be continued according to the customary methods.

By way of verification, a comparative electrophoresis of the plasmid solutions obtained after alkaline lysis, either in a continuous stream (as described in the above example) or by manual stirring for 10 min (the quantities of bacteria used in both cases were similar), was carried out. The staining of the electrophoresis gel demonstrates the superiority of the continuous method since the content of plasmids is increased and that of the impurities is lower.

What is claimed is:

1. A method of cell lysis comprising combining nucleated cells and a lysing agent to produce a liquid mixture and causing the mixture to flow in a steady stream inside a tube having an internal diameter of about 1 cm or less at a temperature of $\leq 60°$ C., wherein the flow rate of the stream is adjusted as a function of the diameter and of the length of the tube so as to obtain a substantially homogeneous cell lysate at the outlet of the said tube, and wherein at or after the meeting point of the nucleated cells and the lysing agent, a device employing a baffle or an obstacle in tubing is not employed.

2. The method according to claim 1, wherein the diameter of the tube is 2 to 8 mm.

3. The method according to claim 1, wherein the mixing of cells and of lysing agent is conducted by introducing into the tube a stream of a suspension of cells and a stream of a solution of lysing agent.

4. The method according to claim 1, wherein the lysing agent is an alkaline lysing agent.

5. The method according to claim 4, wherein the lysing agent is a sodium hydroxide/SDS mixture.

6. The method according to claim 4, wherein a alkaline lysing agent is added to the cell lysate at the end of the tube.

7. The method according to claim 6, wherein the alkaline lysing agent is sodium or potassium acetate.

8. The method according to claim 1, wherein the lysing agent is a hypotonic solution.

9. A method of extracting plasmid DNA from cells containing the DNA, the method comprising:
   (i) producing a cell lysate according to the method of claim 1;
   (ii) treating the cell lysate with a precipitating, a neutralizing, or a precipitating and neutralizing agent to obtain a preparation comprising (a) a supernatant containing the plasmid DNA and (b) a precipitated or flocculated phase containing the majority of the cellular components, including the genomic DNA.

10. The method of extraction according to claim 9, wherein:
   (i) establishing a stream of the cell suspension in a first tube;
   (ii) establishing a stream of the lysing agent in a second tube that flows into the first tube (or vice versa) at a first meeting point to form a third tube;
   (iii) establishing a stream of a precipitating agent in a fourth tube that flows into the third tube (or vice versa)

at a second meeting point situated downstream of the first meeting point to form a fifth tube;

(iv) establishing a stream of the cell/lysing agent mixture produced at the first meeting point in the third tube between the first and second meeting point with a flow rate adjusted as a function of the diameter and length of the third tube to allow the homogenization of the mixture and the production of a substantially homogeneous cell lysate at the second meeting point;

(v) establishing a stream from the second meeting point in a fifth tube by mixing the cell/lysing agent mixture of the third tube with the precipitating agent of the fourth tube;

and (vi) recovering a preparation comprising a supernatant containing the plasmid DNA and a precipitated or flocculated phase containing the majority of the cellular components, including the genomic DNA, from the fifth tube.

11. The method according to claim 10, wherein the length of the tube between the first and second meeting point is from about 10 cm to a few meters.

12. The method according to claim 9, wherein the precipitating, neutralizing, or precipitating and neutralizing agent is sodium or potassium acetate.

13. The method according to claim 9, further comprising separation of the supernatant from the precipitated or flocculated phase.

14. The method according to claim 1 or 9, wherein the cells are bacterial.

15. The method according to claim 1 or 9, wherein the cells are eukaryotic cells.

16. An apparatus for carrying out the method according to claim 1, the apparatus comprising:

(i) a first tube for establishing a stream of cell suspension in fluid connection with a cell suspension source, (ii) a second tube for establishing a stream of lysing agent in fluid connection with a source of lysing agent, the first and second tubes ending at a first meeting point at which they open into each other, (iii) a third tube having an internal diameter of about 1 cm or less and a length between about 10 cm to about a few meters extending from and in fluid connection with the first meeting point, and (iv) one or more devices for establishing the streams in the said first, second and third tubes;

wherein the length, the diameter, and the flow rate in the third tube provides a substantially homogeneous mixture resulting in a substantially homogeneous lysate.

17. The apparatus according to claim 16, further comprising:

(i) a fourth tube in fluid connection with a neutralizing, precipitating, or neutralizing and precipitating agent source at one end and in fluid connection with the second meeting point such that the third tube and the fourth tube open into each other, the third tube having a length determined by the distance between the first meeting point and the said second meeting point;

(ii) a fifth tube in fluid connection with the second meeting point and having a small diameter ending at a recovery and/or separation means; and (iii) a device for establishing the streams in the fourth and fifth tubes.

18. The apparatus according to claim 16, wherein the device is a pump.

19. The method according to claim 10 wherein the internal diameter of the third tube is 2 to 8 mm.

20. The method according to claim 10 wherein the internal diameter of the fifth tube is 2 mm to 1 cm.

21. The method according to claim 10 wherein the internal diameter of both the third and fifth tubes is 2 to 8 mm.

22. The apparatus according to claim 16 wherein the third tube has an internal diameter of 2 to 8 mm.

23. The apparatus according to claim 17 wherein the fifth tube has an internal diameter of 2 mm to 1 cm.

24. The method according to claim 9 wherein the diameter of the tube is 2 to 8 mm.

25. The method according to one of claim 1–8 wherein the flow rate of the stream is less than 1000 ml/min.

26. The method according to claim 9 wherein the flow rate of the stream is less than 1000 ml/min.

27. The method according to claim 10 wherein the flow rates of the streams are less than 1000 ml/min.

28. The method according to claim 11 wherein the flow rates of the streams are less than 1000 ml/min.

29. The method according to claims 14 or 15 wherein the flow rate of the stream is less than 1000 ml/min.

30. The apparatus according to one of claims 16–18 wherein the flow rates of the streams is less than 1000 ml/min.

31. The method of claim 1 wherein the temperature is room temperature.

32. The method of claim 1 wherein said combining of cells and lysing agent and said causing the mixture to flow in a steady stream inside a tube are done continuously.

* * * * *